United States Patent

Higaki et al.

[11] Patent Number: 5,980,833
[45] Date of Patent: Nov. 9, 1999

[54] CARBON MONOXIDE SENSOR

[75] Inventors: Katsuki Higaki, Sakai; Shuzo Kudo, Ikoma; Hisao Ohnishi, Osaka; Soichi Tabata, Hirakata; Osamu Okada, Osakasayama; Yosuke Nagasawa, Osaka, all of Japan

[73] Assignee: Noritsu Koki Co. Ltd, Wakayama, Japan

[21] Appl. No.: 08/883,785

[22] Filed: Jun. 27, 1997

[30] Foreign Application Priority Data

Jun. 28, 1996 [JP] Japan .................................. 8-169029
Jun. 28, 1996 [JP] Japan .................................. 8-169030
Jun. 28, 1996 [JP] Japan .................................. 8-169031
Oct. 3, 1996 [JP] Japan .................................. 8-262683
Apr. 8, 1997 [JP] Japan .................................. 9-89090

[51] Int. Cl.$^6$ .................................................. G01N 29/00
[52] U.S. Cl. ........................... 422/98; 436/134; 436/137; 436/145; 436/149; 436/153; 428/697; 428/902; 428/704
[58] Field of Search ..................... 204/421, 424; 205/782, 784, 784.5, 785.5; 73/23.2, 23.31, 31.05, 31.06; 338/34; 422/40, 94–98, 83; 436/134, 137, 145, 149, 153; 427/126.2, 126.3; 428/697, 902, 704

[56] References Cited

U.S. PATENT DOCUMENTS

| | | | |
|---|---|---|---|
| 4,194,994 | 3/1980 | Baresel et al. | 252/518 |
| 5,252,949 | 10/1993 | Kirby et al. | 340/632 |
| 5,346,671 | 9/1994 | Goswami et al. | 422/86 |
| 5,351,029 | 9/1994 | Huth et al. | 338/34 |
| 5,362,651 | 11/1994 | Soltis et al. | 436/134 |
| 5,382,341 | 1/1995 | Arovtiounian et al. | 204/192.21 |
| 5,734,091 | 3/1998 | Kudo et al. | 73/23.2 |

FOREIGN PATENT DOCUMENTS

| | | |
|---|---|---|
| 6632265 | 1/1995 | European Pat. Off. . |
| 3024449 | 1/1982 | Germany . |
| 5343320 | 11/1978 | Japan . |
| 5332972 | 12/1993 | Japan . |

OTHER PUBLICATIONS

The Chemical Society of Japan ©1991; Chemistry Letter, pp. 1759–1762, 1991; Gas Sensing Characteristics of Superconducting Cuprates; E Grantscharova, A Raju, CN Rao; Materials Research Centre and Jawaharlal Nehru Centre for Adv. Sci. Res., Indian Inst. of Sci., Bangalore–560 012, India.

Co–pending U.S. Serial No. 08/805, 037 filed Feb. 21, 1997.

Dialog(R) File 351: Derwent WPI; Title: Semiconductor Sensor for Determination of Oxygen in Exhaust Gas; Assignee: Robert Bosch GmbH; Inventor: D Baresel, G Huth, P Scharner; Patent No. De 3024449A; Derwent Class: E36; Intl Class: G01N–027/12.

Niu et al. "Periodicity Change in Structural Modulation in $Bi_2Sr_2Ca_{1-4}Re_4$ $Cu_2O_8$ & (RE=4, Nd) System" Japanese Journal of Applied Physics, vol. 28, No. 5, May 1989, pp. 784–786.

Huang et al. "High To Superconductors as $NO_x$ and $CO_x$ Sensor Materials" Solid State Ionics 57 (1992) pp. 7–10.

*Primary Examiner*—Jill Warden
*Assistant Examiner*—S. Carrillo
*Attorney, Agent, or Firm*—Fulbright & Jaworski, LLP

[57] ABSTRACT

A carbon monoxide sensor including a gas detecting portion and at least a pair of electrodes, wherein the gas detecting portion includes a metal oxide represented by a following formula;

$$Cu_{1-x}Bi_xO_y$$

(0<x<1 and 1<y<1.5).

10 Claims, 9 Drawing Sheets

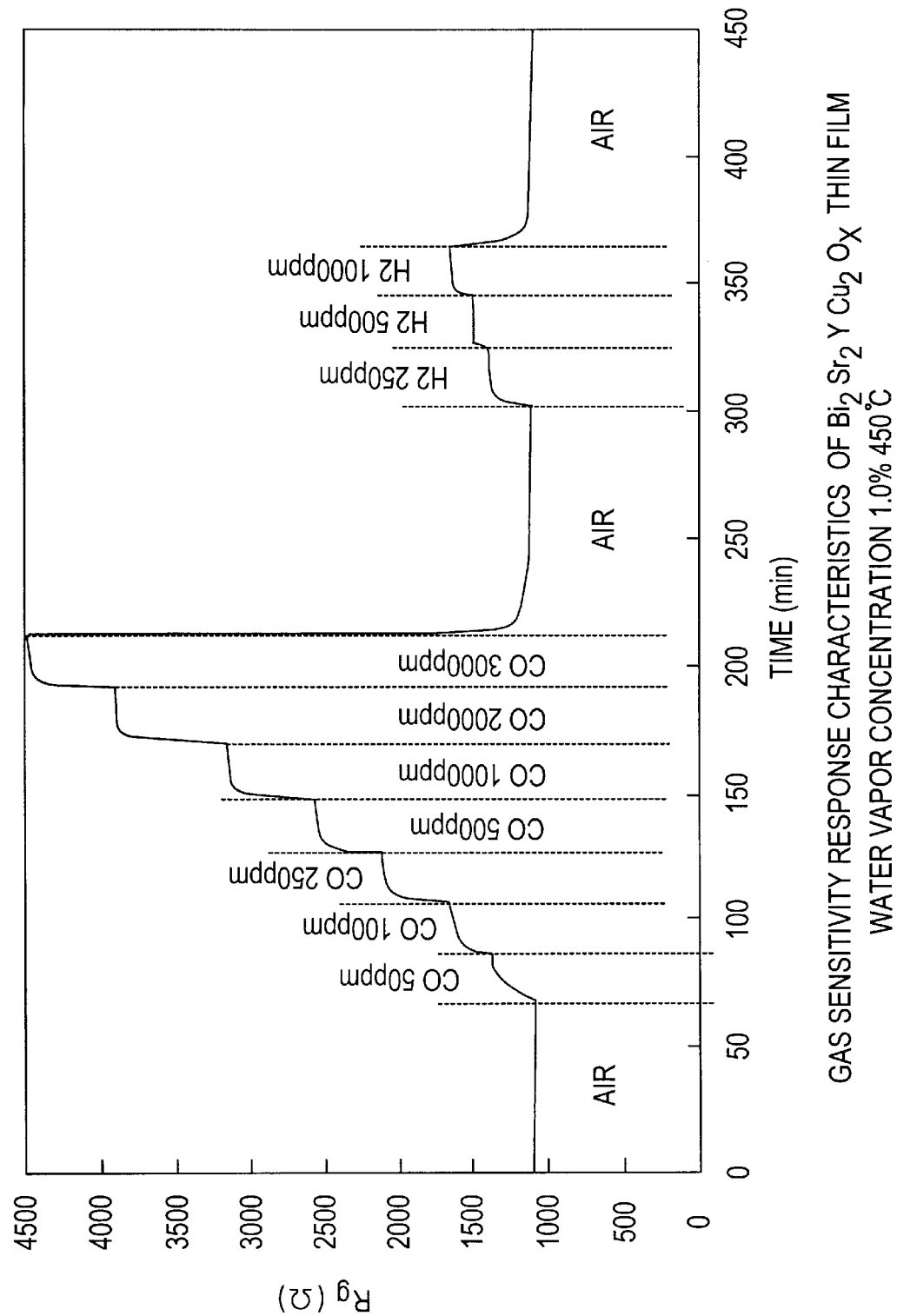

CARBON MONOXIDE SENSOR

FIELD OF THE INVENTION

The present invention relates to a carbon monoxide sensor for detecting concentration of carbon monoxide present in atmosphere.

Description of the Related Art

As is well-known, carbon monoxide, CO, is a substrate present in the form of gas in a normal temperature and having combustibility as well as high toxicity against human body. On the other hand, CO is an important raw material is chemical industries and is generated from combustion of carbonaceneous fuel. The concentration of CO which adversely affects the human body is much lower than the explosion-limit concentration thereof. For these reasons, there has been constant demand for a carbon monoxide sensor of ever higher sensitivity.

In the carbon monoxide sensors of practical use, there is known a type using semiconductor metal oxide material adapted to gas concentration detection at a relatively low temperature (see Japanese published patent gazette Sho. 53-43320). More particularly, this sensor actually employs tin oxide as the metal material.

However, such conventional carbon monoxide sensor based on tin oxide has the following problems:

a) necessity of periodical heating;
b) relatively slow response;
c) saturation of sensitivity at high CO concentration range. In other words, at the high gas concentration range, the sensor can provide only limited sensitivity variation in response to gas concentration variation. Hence, the quantitative performance of the sensor is poor;
d) relatively poor sensitivity at low CO concentration range.

These problems will be discussed next in greater details with reference to a response curve depicted in a graph of FIG. 9, which illustrates the sensitivity of such currently commercially available carbon monoxide sensor based on tin oxide relative to CO and $H_2$.

In FIG. 9, the vertical axis represents the sensor output (V) and the horizontal axis represents the time (min.). In this graph, the types and concentrations of the detection target gases are respectively denoted at positions corresponding vertically relative to the detection curve. Incidentally, FIGS. 2, 6 and 8, to be referred to later, employ the same method of graphic illustration as FIG. 9. Hence, these graphs are to be considered in comparison with each other.

Next, the respective problems of the conventional sensor will be discussed specifically.

a) necessity of periodical heating:

At a relatively high temperature range (normally, 450° C.), this sensor has substantially same sensitivity for CO and $H_2$. On the other hand, at a lower temperature range around 100° C., the sensor is capable of detecting CO and $H_2$ distinctly from each other. However, if the sensor is maintained at such low temperature for an extended period of time, there occurs reduction in the sensor sensitivity due to e.g. ambient moisture. Therefore, it is necessary to periodically heat the sensor so as to remove therefrom water vapor which tends to be adsorbed by the sensor under the low temperature. Then, for effecting CO detection in an environment in which both CO and $H_2$ are present, the ambient temperature of the sensor is alternatively elevated and lowered periodically, and the sensor is capable of selectively detecting CO when the temperature is low.

For the above reasons, the sensor provides a jagged detection curve as shown in FIG. 9. In this, the detection value at the bottom between the adjacent 'hills' of the jagged curve is used as the effective CO detection value for each gas concentration.

b) slow response:

Because of the necessity of periodical heating described above and also because of its own inherent characteristics, the response performance of this conventional sensor is poor. For instance, such poor response performance of the sensor may be seen in the data of FIG. 9 at the range of 500 ppm of CO, which range is generally considered to be of vital importance.

c) sensitivity at high CO concentration range:

The 'high concentration range' here denotes a gas concentration range exceeding 500 ppm approximately. In the CO detection values shown in FIG. 9, there develops the tendency of sensitivity saturation with increase in the CO concentration. Hence, the sensitivity of the sensor becomes poorer.

d) poor sensitivity at low CO concentration range:

The 'low concentration range' here denotes a range below 50 ppm approximately. In the CO detection values shown in FIG. 9, the sensor outputs values of small magnitudes, hence, the sensor sensitivity is poor in such low concentration ranges too.

In addition to the above-described type, the convention has proposed a further CO sensor including a gas detecting portion having a composition disclosed in U.S. Pat. No. 5,362,651. However, this sensor too has room for improvement in its CO sensitivity and selectivity between CO and $H_2$.

Therefore, in view of the above-described state of the art, a primary object of the present invention is to provide a carbon monoxide sensor capable of solving the above problems of the conventional CO sensors.

SUMMARY OF THE INVENTION

For accomplishing the above noted object, in a carbon monoxide sensor including a gas detecting portion and at least a pair of electrodes, according to the present invention, the gas detecting portion is comprised mainly of metal oxide represented by a following Formula 1;

$$Cu_{1-x}Bi_xO_y$$

(0<x≦1: y is determined by x). (this composition will be referred to as Composition 1 hereinafter). In a preferred embodiment, 0<x<1 and 1<y1.5.

The present inventors has discovered that the sensor including a gas detecting portion comprised mainly of the material having the above-described composition provides a resistance value which varies in good response to CO concentration variation as well as superior selectivity for CO against $H_2$.

This sensor can be used continuously in a relatively high temperature range where the sensor may be protected against disturbing effect of e.g. ambience moisture. Then, this sensor is capable of effecting CO detection without necessitating periodical and alternate ambience temperature lowering and elevating operations. Also, with this sensor, the output resistance value of its gas detecting portion increases substantially linearly in response to increase in CO concentration, and this resistance variation is of such magnitude that it is still detectable at the low concentration range of 50 ppm or lower. Moreover, the sensor response speed is superior to that of the convention using tin oxide. Further, this sensor has origin reversibility (i.e. the ability to return to the origin immediately with disappearance of CO).

However, in the case of pure copper oxide semiconductor, i.e. x=0, the sensor sensitivity for $H_2$ becomes higher than that for CO. Therefore, this is not preferred.

According to one preferred embodiment of the present invention, in the carbon monoxide sensor having the above-described construction, the gas detecting portion is provided in the form of a thin film comprised mainly of a metal oxide represented by a following Formula 2, the film having a thickness smaller than 1 μm (this composition will be referred to as Composition 2 hereinafter).

$Bi_2Sr_2(Ca_aY_b)Cu_2O$ $(0 \leq a \leq 1, 0 < b \leq 1)$

The present inventors have discovered that the sensor including a gas detecting portion comprised mainly of the material having the above-described composition provides a resistance value which varies in good response to CO concentration variation as well as superior selectivity for CO against $H_2$. Moreover, by forming the film in the thickness of 1 μm or smaller, the sensitivity for CO as well as the selectivity against $H_2$ may be further improved. In this respect, in the case of zero substitution by Y, in comparison with the presence of at least some substitution by Y, the sensor sensitivity for CO is lowest, and so is the selectivity for CO against $H_2$.

With this sensor too, the output resistance value of tis gas detecting portion increases substantially linearly in response to increase in CO concentration, and this resistance variation is detectable at the low concentration range of 50 ppm or lower. Moreover, the sensor response speed is superior to that of the convention using tin oxide.

However, if Ca is not substituted for at all by Y (i.e. b=0), the sensor sensitivity for CO becomes closer to that for $H_2$, and therefore this is not preferred.

According to a further embodiment of the present invention, in a carbon monoxide sensor including a gas detecting portion and at least one pair of electrodes, the gas detecting portion is comprised mainly of copper oxide semiconductor added with a metal compound belonging in group 2A of the period table (this composition will be referred to as Composition 3 hereinafter).

It has been known in the art that copper oxide semiconductor has sensitivity for CO. However, this sensitivity is inferior to that of tin oxide. Further, copper oxide semiconductor has sensitivity also for $H_2$. Accordingly, with this semiconductor, it has been impossible to obtain sufficient selectivity for the target CO gas. For this reason, there has been less attention on the copper oxide semiconductor as a CO sensing material. However, the present inventors have discovered that with addition of a metal compound in the group 2A of the periodic table to this copper oxide, the selectivity for $H_2$ may be effectively restricted to a degree not to affect its CO detection, thus achieving the above invention.

Unlike the conventional sensors, this sensor too does not require the periodic temperature lowering and elevating operations. And, this sensor is capable also of selectively detecting CO against $H_2$ even in the relatively high temperature condition, thus achieving sufficient CO sensitivity at such high temperature range as well as at the low concentration range. Moreover, this sensor has good origin reversibility to return to its origin when CO becomes absent.

Preferably, in the carbon monoxide sensor described above, the metal compound belonging in the group 2A to be added to the copper oxide semiconductor comprises at least one kind of alkaline earth metal selected from the group consisting of barium, strontium and calcium.

Such compounds can effectively restrict the $H_2$ sensitivity of the copper oxide semiconductor.

Preferably, these group-2A metal compounds are present in the gas detecting portion as more than one phase of oxide compound with oxide, hydroxide, carbonate or copper.

Still preferably, the composition of the group-2A metal compound to be added to the copper oxide semiconductor used in the gas detecting portion is such that the metal compound is present in an equivalent weight ratio: $0 < d/Cu \leq 2.0$, where 'd' is an equivalent weight of the group 2A metal contained in the metal compound relative to copper.

Without the addition of the group-2A metal compound, there will occur increase of the $H_2$ sensitivity of the gas detecting portion and this $H_2$ sensitivity will eventually become higher than the CO sensitivity. On the other hand, if the equivalent weight ratio of the group-2A metal oxide exceeds 2.0; then, although the $H_2$ sensitivity may still be maintained low, but, this will lead to precipitation of e.g. carbonate having electrically insulating property, thus increasing the resistance value of the sensor. Moreover, the carbonate will absorb moisture, thereby rendering the gas detecting portion fragile. Therefore, such excessive addition more than 2.0 will be undesirable.

In the carbon monoxide sensor described above, the detecting portion is preferably provided as a thin film formed on a substrate.

In the case of the Compositions 1 and 3 described above, the gas detecting portion may be fabricated by the well-known sintering method. In the case of this sintering method, the gas detecting portion is sintered on the substrate, thereby to affix the gas detecting portion on the substrate simultaneously with the sintering process. Alternatively, the gas detecting portion may be sintered in advance and then be affixed to the substrate. Furthermore, in order to increase the physical strength of the gas detecting portion, binder material exerting no effect on the sensor sensitivity may be used in the material for forming the gas detecting portion. Such addition of binder material will be useful and effective also in the thin film type construction described hereinbefore.

According to a still further embodiment of the present invention, the gas detecting portion further includes a catalyst layer for preventing non-target gas (i.e. any other gas than the target CO gas) from reaching the gas detecting portion. With presence of such catalyst layer, it is possible to eliminate disturbing effect of such non-target gases as hydrocarbon gas generated as a product of incomplete combustion. Then, the CO selectivity of the sensor may be further improved.

In the sensor construction of the present invention, it is preferred that the gas detecting portion may be heated by heating means such as a heater attached to the substrate. However, it is also conceivable to provide e.g. a coil heater inside the detecting portion of the sensor incorporating the gas detecting portion. With such arrangements, it becomes possible to maintain constant the temperature of the gas detecting portion and also to set the portion to an optimum temperature condition where its sensitivity is highest.

The heating may be effected so as to adjust and maintain the gas detecting portion at a predetermined temperature. And, the heating means may be embedded within the substrate. Or, the heater may be provided in the form of a layer attached to the substrate or affixed to one side of the substrate. Further, alternatively, the heating means may be adapted to heat the periphery of the substrate.

Further and other features and advantages of the invention will become more apparent from the following detailed description of the invention with reference to the accompanying drawings.

BRIEF DESCRIPTION OF THE DRAWINGS

FIG. 6 is a graph illustrating CO and $H_2$ response characteristics of the sensor including the sensor detecting portion having the Composition 2 according to the invention.

DESCRIPTION OF THE PREFERRED EMBODIMENTS

Figure 1:
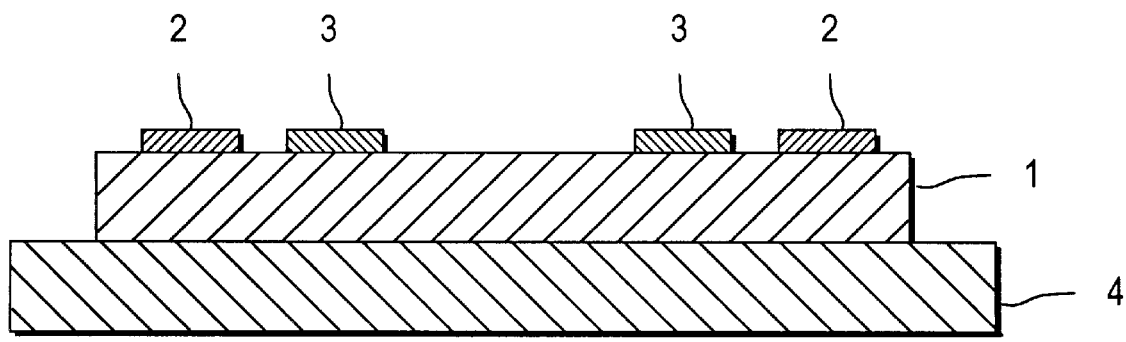
FIG. 1 is a schematic showing a construction of a sensor relating to the present invention.

A carbon monoxide sensor, to which the present invention relates, generally includes a gas detecting portion and at least one pair of electrodes electrically connected with the gas detecting portion. More particularly, as shown in FIG. 1, the sensor includes a gas detecting portion 1 provided in the form of a bulk or film comprised of a material having a predetermined composition according to the invention and pairs of electrodes 2 and 3 attached to a surface of the gas detecting portion 1. In operation, the sensor detects carbon monoxide through detection of an electric property between these electrodes pairs. Usually, the paired electrodes 2 are used for applying electric current, while the other paired electrodes 3 are used for detecting developed electric potential. The gas detecting portion 1, which is the main component of this carbon monoxide sensor, is formed on a substrate 4, which in turn includes a heater for heating the gas detecting portion 4.

In case the gas detecting portion 1 is provided in the form of a bulk-like portion, the so-called sintering method may be employed. Then, powdery starting materials are mixed in a predetermined mixture ratio and then sintered together for obtaining the target material. Further, in fabricating this gas detecting portion, by additionally using binder material which does not affect the sensor sensitivity, the physical strength of the sintered product may be improved advantageously.

On the other hand, in case of the gas detecting portion 1 is provided in the form of a thin film, as the method for forming this thin film, any of the chemical vapor deposition method such as the heat CVD, plasma CVD and laser CVD method, or physical vapor deposition method such as vacuum vapor deposition method, sputtering method and laser ablation method may be implemented. In the case e.g. of the Composition 2 of the invention where the film thickness is to be controlled, such method as cited above may be employed. In this case too, binder material not affecting the sensor sensitivity may be additionally used for increasing the physical strength of the gas detection portion 1.

As the material for forming the gas detecting portion 1 of the sensor, the present invention proposes the following three kinds of compositions, namely, the Composition 1 of $Cu_{1-x}Bi_xO_y$ (0<x≦1: y is determined by x), Composition 2 of $Bi_2Sr_2(Ca_aY_b)Cu_2O_{8-c}$ (0≦a≦1, 0<b≦1), and the Composition 3 of copper oxide semiconductor added with a metal compound belonging in the group 2A of this periodic table.

Next, embodiments using the above respective compositions will be described in greater detail.

1. Embodiment of Composition 1 ($Cu_{1-x}Bi_xO_y$)

[example method of fabricating the gas detection portion]

Commercially available copper oxide (CuO) of high purity and bismuth ($Bi_2O_3$) are used. And, these materials in the form of powder are mixed in a predetermined Bi/(Bi+Cu) ratio or Cu/Bi ratio. Then, this mixture is preliminary sintered and the sintered product is pulverized. Thereafter, this powder product is pressurized and molded into a predetermined shape and then heated and sintered on an alumina ($Al_2O_3$) substrate at 600 to 750° C., whereby the gas detecting portion is obtained.

Incidentally, in this embodiment, the mixing ratio (equivalent weight ratio) is represented in the form of either Bi/(Bi+Cu)=x or Bi/Cu=z ratio. These values may be obtained by the following expression, Formula 3:

$$x=z/(1+z)$$

$$(z=Bi/Cu)$$

With increase of the ratio of Bi, the melting point of the raw material mixture obtained by the sintering becomes lower. Specifically, the mixture composition of $CuO/Bi_2O_3$= 1/1 is about 670° C. On the other hand, in general, the more porous the substrate is, the higher the sensitivity of the gas detecting portion becomes. Thus, it is preferred that the gas detecting portion including a high ratio of $Bi_2O_3$ be sintered at a relatively low temperature.

The crystal structure of the gas detecting portion obtained as described above was analyzed through the X-ray diffraction analysis. According to the analysis, when the addition amount of Bi is 0.05 or less, no X-ray diffraction detection was possible due to the small amount of Bi and the single phase of CuO was detected. On the other hand, when the amount was within a range between 0.05 and 2.0, phases of CuO, $CuBi_2O_4$ and a trace amount of $Bi_2O_3$ were detected. Further, in case the amount was greater than 2.0, phases of $CuBi_2O_4$ and $Bi_2O_3$ were detected.

[fabrication of the sensor]

On the surface of the gas detecting portion of the sintered material obtained as above, the electrodes 2, 3 were formed of platinum, as shown in FIG. 1.

[measurement of sensitivity]

Target gas for detection was obtained by mixing CO and $H_2$ in predetermined concentrations with air. Further, there was used another target gas including a predetermined amount of water vapor in addition to the above. These target gases had an oxygen concentration of about 20% and was dry to have a moisture of 1, 1.5%.

In the measurement conducted, a predetermined electric potential was applied to the heating substrate to heat and maintain the gas detecting portion at 250 to 450° C. And, gas concentration detection was made by measuring electric resistance developed between the opposed electrodes. The gas sensitivity (S) was claimed from a following expression;

$$S=Rg/Rair$$

where, Rair denotes a resistance value when the sensor was placed into contact with air which does contains neither CO nor $H_2$. Rg denotes a resistance value when the sensor was place into contact with the target gas. S=1 means no detection of the gas component.

Figure 2:
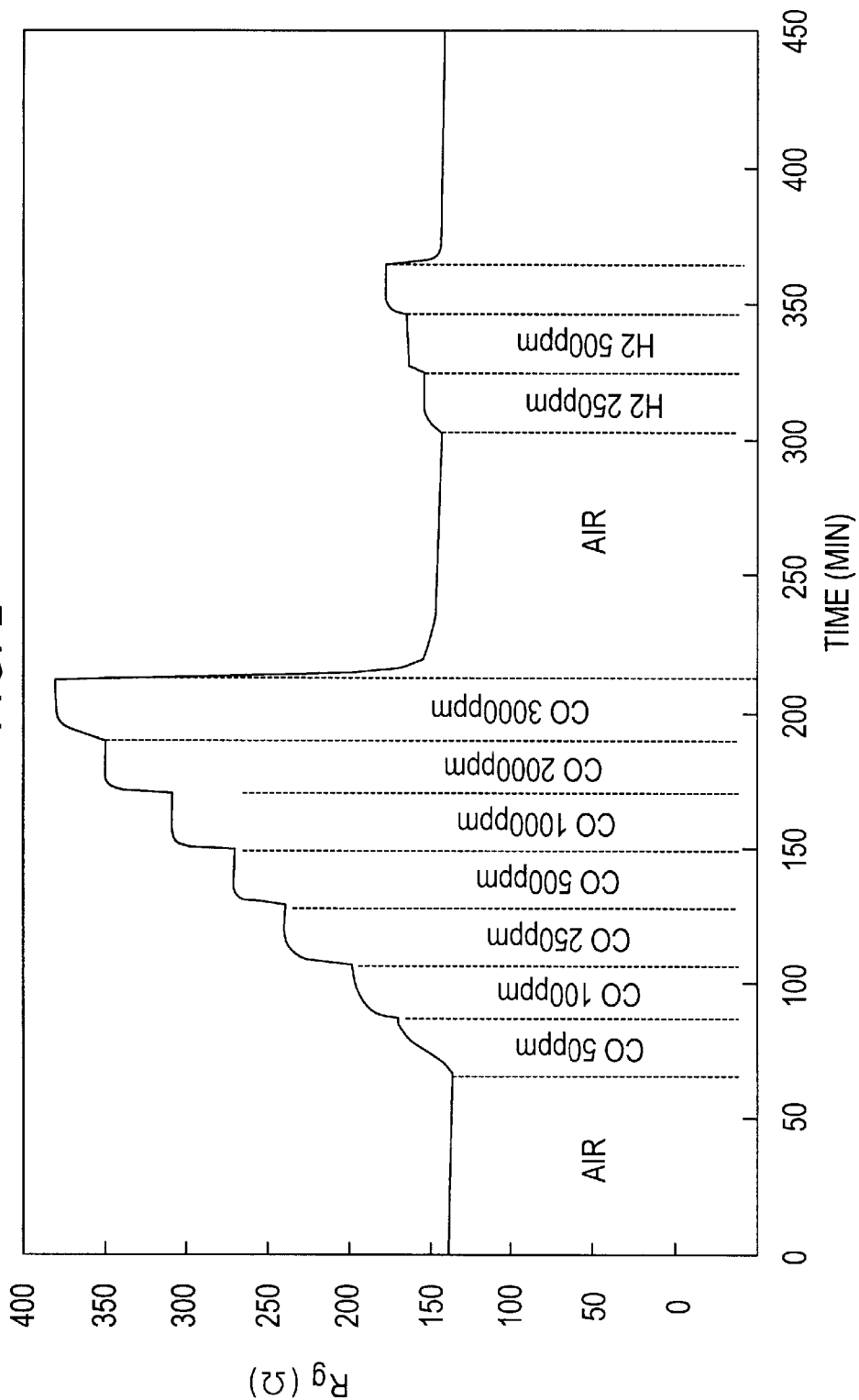
FIG. 2 is a graph showing CO and $H_2$ response characteristics of a sensor including a gas detecting portion having the Composition 1 according to the invention.
Figure 3:
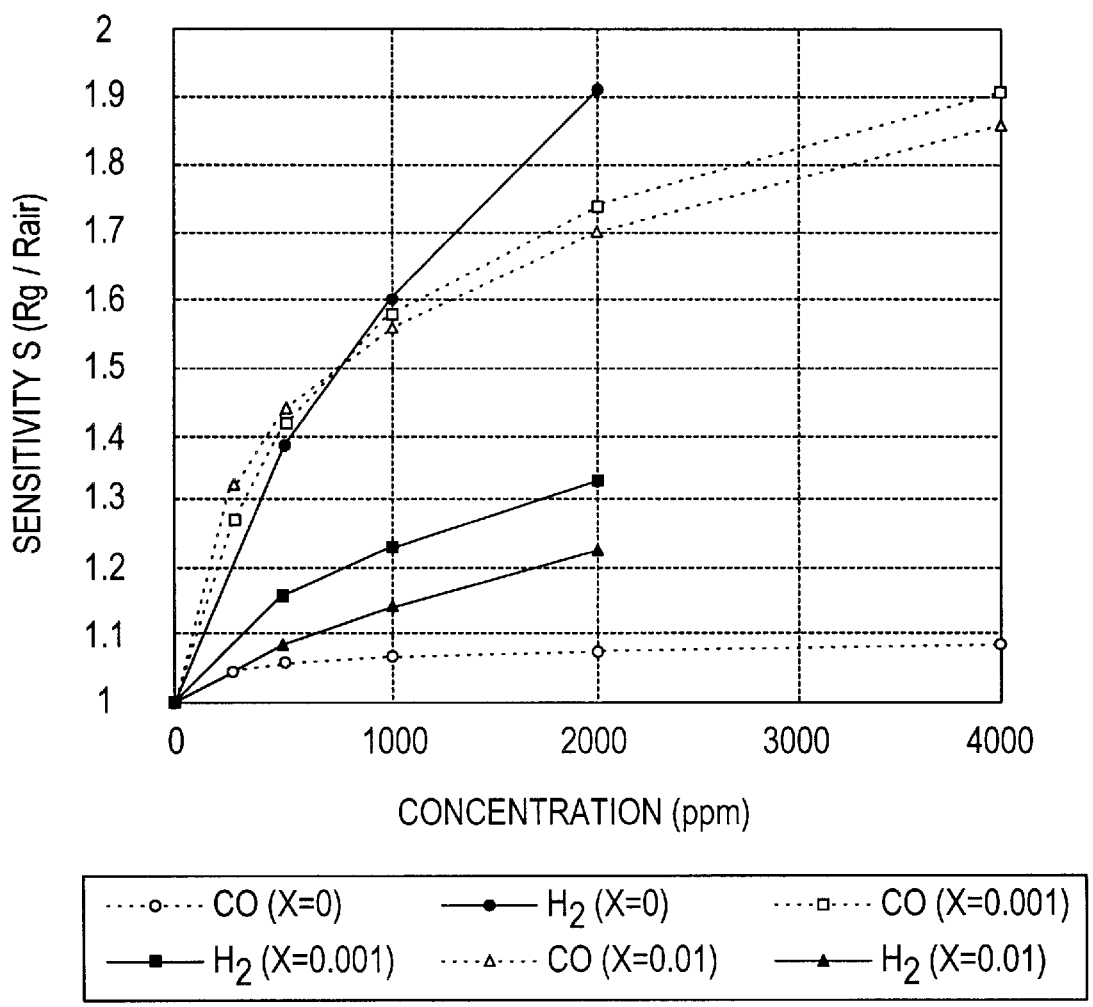
FIG. 3 is a graph illustrating dependence of sensitivity S of a sensor including a gas detection portion having a composition of Bi ratio 'x' ranging between 0 and 0.01 on CO and $H_2$ concentration variations.
Figure 4:
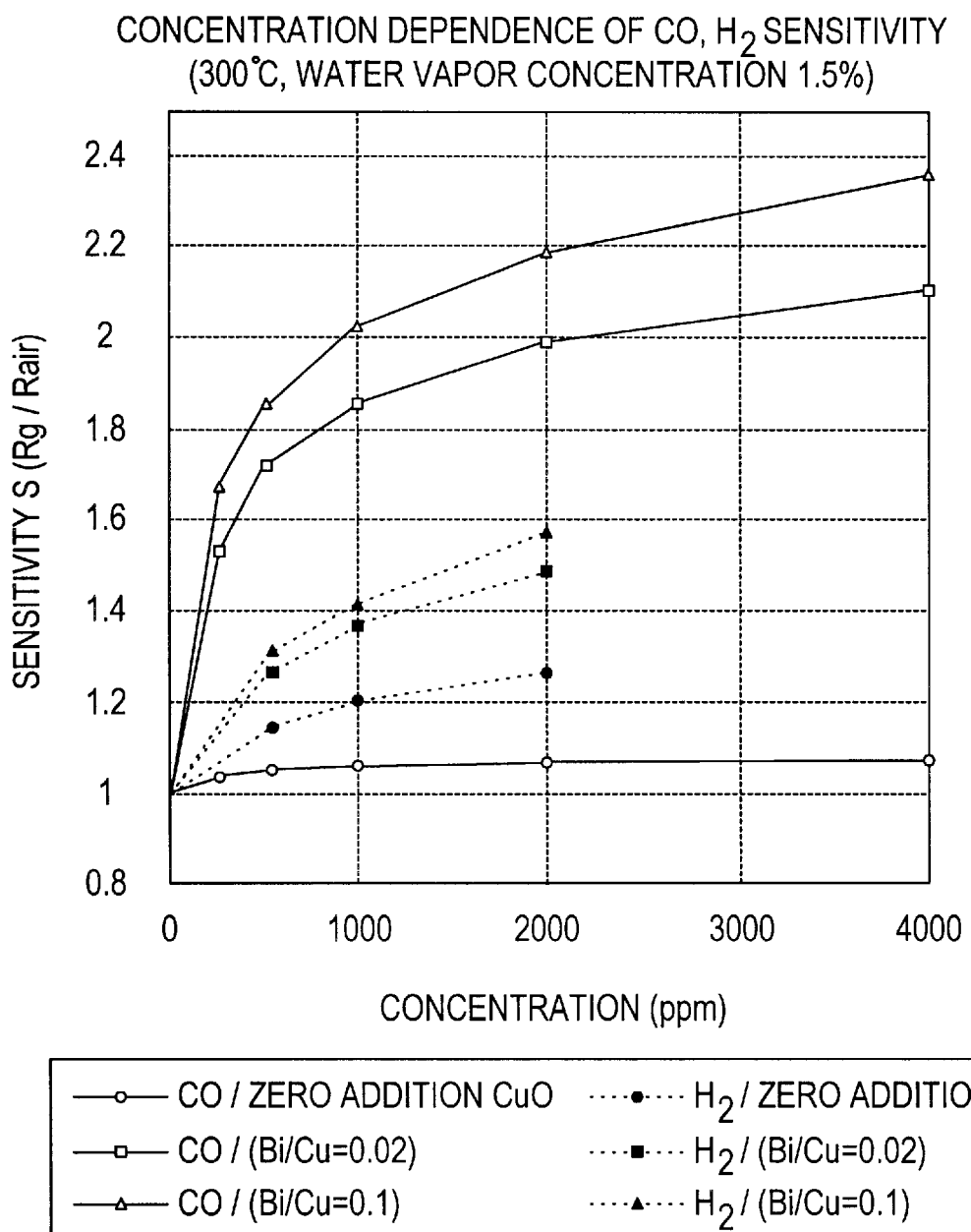
FIG. 4 is a graph illustrating dependence of sensitivity S of a sensor including a gas detecting portion having a composition of a Bi/Cu ratio being 0, 0.02 and 0.1 on CO and $H_2$ concentration variations.

The results are summarized and shown in Table 1 and FIGS. 2 through 4.

Table 1 shows the results of measurement of the sensitivity of the gas detecting portion in which the ratio of Bi (i.e. the value of x in formula 3) was varied for the gas having 1000 ppm CO concentration and 1000 ppm $H_2$ concentration.

TABLE 1

| | sensor sensitivity | |
|---|---|---|
| x | CO(1000 ppm) | $H_2$(1000 ppm) |
| 0 | 1.06 | 1.60 |
| 0.001 | 1.57 | 1.23 |
| 0.002 | 1.58 | 1.12 |
| 0.005 | 1.51 | 1.10 |
| 0.01 | 1.56 | 1.14 |
| 0.02 | 1.48 | 1.08 |
| 0.04 | 1.60 | 1.11 |
| 0.05 | 1.50 | 1.32 |
| 0.667 | 1.29 | 1.20 |
| 0.8 | 1.30 | 1.20 |
| 1.0 | 1.57 | 1.40 |

From the results shown in Table 1 above, it may be seen that the sensor having the gas detecting portion comprised solely of copper oxide has lower sensitivity for CO than for $H_2$ but that the sensors having the gas detecting portions comprised of oxide containing Bi and bismuth oxide both have high sensitivity for CO. Further, if the effect of e.g. moisture is considered, it is preferred that 'x' is greater than 0 (excluding 0 per se) and smaller than 0.5.

FIG. 2 illustrates the response and the dependence of CO concentration and $H_2$ concentration of the resistance value variation of the sensor using a gas detecting portion having the ratio of bismuth used, i.e. Bi/CuO (Formula 3), of 4/96. The measurement conducted on target gas having water vapor concentration of 1% at 300° C. In this measurement, no periodic heating/cooling was done.

As shown, it may be seen that the sensor of the invention is capable of detecting CO without necessitating any periodic heating operation and provides good sensitivity at the high gas concentration range (i.e. the detection value varies in proportion to the logarithmic value of the gas concentration) and also good sensitivity (resistance value variation) at the relatively low gas concentration range.

Moreover, with this sensor, its sensitivity for $H_2$ is small, and the selectivity against $H_2$ may be maintained at a high temperature where the effect of moisture is negligible.

FIG. 3 illustrates the response and the dependence on CO concentration and $H_2$ concentration of the resistance value variation of the sensor using a gas detecting portion having the ratio of bismuth used, i.e. x in Formula 3 ranging between 0 and 0.01. The measurement was conducted on target gas under dry condition at 300° C. In this measurement, no periodic heating/cooling was done. The results show that the sensor including the gas detecting portion using CuO alone was high sensitivity for $H_2$, but the sensor including the gas detecting portion containing also Bi can achieve the intended object of the present invention.

FIG. 4 illustrates variation of the sensitivity S in response to variation of CO and $H_2$ concentrations of a sensor using a gas detecting portion having the composition Bi/Cu=0, 0.02, 0.1. The target gas used in this measurement had a temperature of 300° C. and an absolute water vapor concentration of 1.5%.

From this result too, it may be seen that except for the results of Bi/Cu=0, the sensor using the gas detecting portion according to the invention has higher sensitivity for CO than for $H_2$ and this sensitivity S increases with increase in the gas concentration and also that the further sensor using a gas detecting portion not containing Bi has higher sensitivity for $H_2$ than for CO thus not suitable for achieving the object of the present invention.

With this sensor of the invention, its sensitivity for CO is higher than that for $H_2$ in the relatively high temperature range where removal of moisture is not necessary, so that this sensor can maintain sufficient gas selectivity for CO at such high temperature range.

2. Embodiment of Composition 2 ($Bi_2Sr_2(Ca_aY_bCu_2O_{8+c})$)

[example method of fabricating the gas detection portion]

The oxide compound for forming the gas detecting portion 1 is obtained according to the following procedure.

First step

Precursor material is obtained from raw material mixture including the elements shown in Formula 2 of the gas detecting portion 1 in a predetermined ratio. In this example, the material used satisfies the relation of a=1−b. In this case, the metal components (Bi:Sr:Ca:Y:Cu) are mixed in a predetermined equivalent weight ratio (2:2:a=1−b:b:2), to obtain the precursor material. The specific examples of the materials including the respective metal elements: Bi:Sr:Ca:Y:Cu are $Bi_2O_3$, $SrCO_3$, $CaCO_3$, $Y_2O_3$, CuO and so on. The value 'b' was set to: 1, 0.8, 0.6, 0.4, 0.2, 0.1, 0.05, 0.01, 0.005 and 0.

Second step

The obtained precursor material is subjected to a preliminary baking and preliminary sintering step, whereby preliminary sintered product is obtained.

In the preliminary sintering step above, the precursor material is sintered at a temperature (780 to 800° C. approximately) lower than a main sintering step, preferably for 48 hours. Then, the preliminary sintered product thus obtained is pulverized to adjust it particle diameter of 1 to 20 μm approximately.

Third step

The resultant preliminary sintered material is subjected to at least two cycles of the main sintering step in a noble gas or carbon gas atmosphere containing 20% or more of oxygen at 810 to 850° C., whereby raw material comprised mainly of metal oxide represented by a following Formula 2 and having 2212 phase crystal structure is obtained;

$$Bi_2Sr_2(Ca_aY_b)Cu_2O_{8+c}$$

(0≤a≤1, 0<b≤1, c is determined by b).

Between the two cycles of the main sintering step, the material is pulverized to adjust its particle diameter to 1 to 20 μm. Further, as the noble gas, argon gas, helium gas or carbon gas is employed. And, the main sintering step is done for at least two cycles at the above-specified temperature range for 24 hours or more. In this case, preferably, the main sintering step is done at least two cycles in argon gas atmosphere containing 20% or more oxygen at a temperature range of 820 to 845° C. for 30 hours or longer.

With the above process, the raw material to be used for a film forming step as follows may be obtained. That is, in case the laser ablation method is employed as is the case with this example, the target of the laser ablation may be obtained.

Fourth step

Using the raw material (target) obtained as above, a film forming method such as the laser ablation method is implemented for obtaining a non-crystalline film having the above-described composition on the substrate 4. The thickness of the film is set to be 1 μm or smaller.

Fifth step (heating step)

The non-crystalline film formed on the substrate is heated at 830 to 950° C. for 20 to 60 minutes. Through this heating step, there is obtained the gas detecting portion 1 comprised mainly of the material whose composition satisfies the above formula and which has the 2212 phase crystalline structure.

[manufacture of the sensor]

To the gas detecting portion 1 obtained as above, the electrodes 2, 3 are attached, and the substrate forming the bottom of the gas detecting portion 1 is used as the heating substrate. Further, if necessary, an oxidizing catalyst layer carrying platinum is attached to the surface side of the gas detecting portion 1. As the base material of the oxidizing catalyst layer, alumina or the like may be employed.

[measurement of sensitivity]

Target gas employed was obtained by mixing air with predetermined concentrations of CO, $H_2$ and methane and also with a predetermined amount of water vapor. The oxygen concentration and the moisture content of this gas were adjusted to about 20% and about 1.5%, respectively.

In the measurement, a predetermined electric potential was applied to the substrate of the gas sensor element thereby to heat and maintain the gas detecting portion 1 to a predetermined temperature range around 400° C. In this condition, the sensor was brought into contact with the target get and an electric resistance developed between the opposed electrodes was measured. Then, the relationship between the variation of this resistance and respective concentrations of the gas was determined.

The gas sensitivity S was determined by the foregoing same expression (Rg/Rair).

Figure 5B:
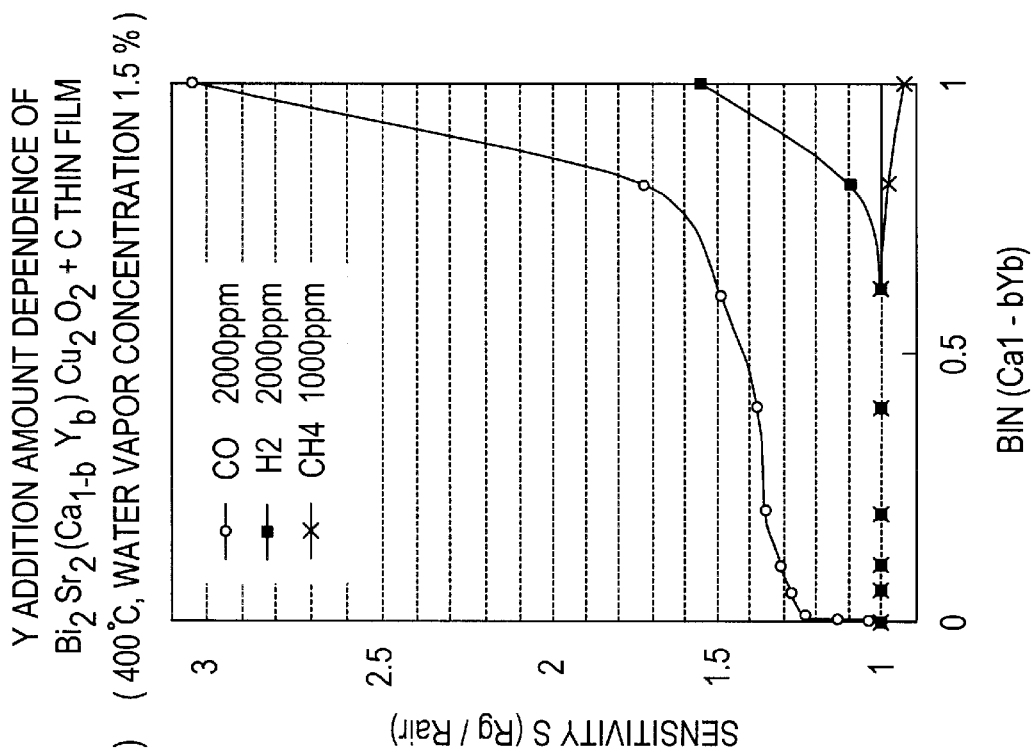
FIG. 5 is a graph showing relationship between Y substitution amount and sensitivity in the case of Composition 2 according to the present invention.
Figure 5A:
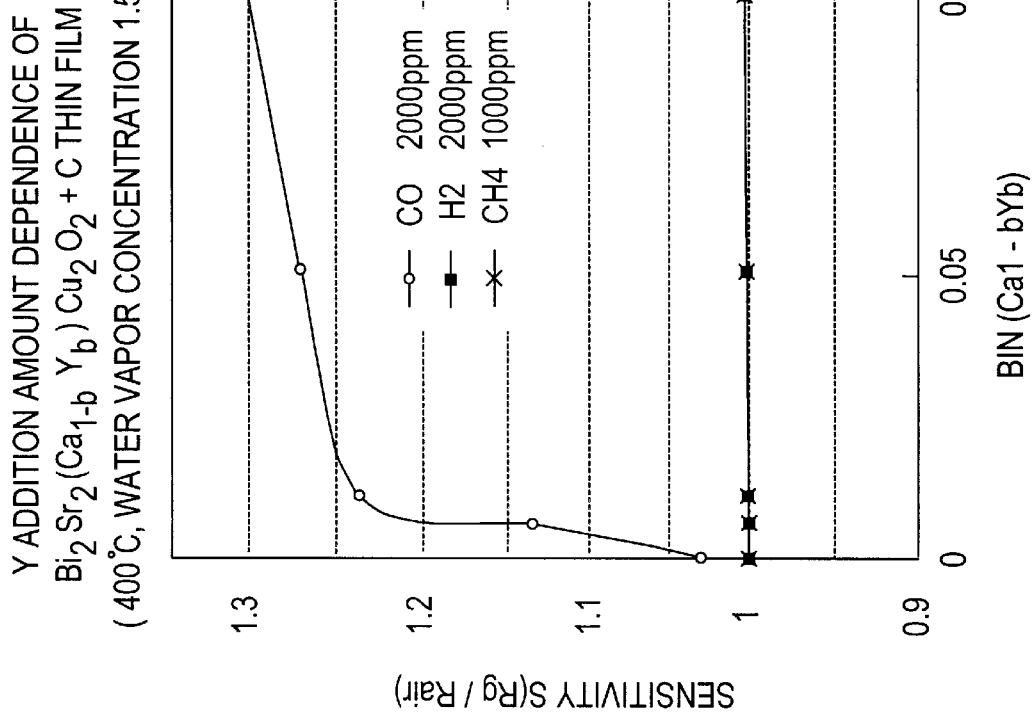

FIG. 5 illustrates the sensitivity values for the respective gas concentrations with varying the substitution amount by Y relative to Ca in the Composition 2. FIG. 5(a) shows the case in which the substitution amount was limited to relatively small values. FIG. 5(b) shows the case in which the substitution amount was varied from zero to 100%. As may be apparent from these results, in the case of this sensor, with increase of the Y substitution amount, the CO sensitivity increases. The one having no Y at all has low selectivity against $H_2$. As may be understood from these graphs, it is preferred that the Y substitution amount be greater than 0.01 and smaller than 1 (more preferably, greater than 0.8 and smaller than 1).

FIG. 6 illustrates the response and dependence on CO concentration and $H_2$ concentration of the resistance value variation of the sensor using the gas detecting portion having a composition of 100% substitution by Y. In this measurement, no periodic heating/cooling was done.

As shown, it may be seen that the sensor of the invention is capable of detecting CO without necessitating any periodic heating operation and provides good quantitative performance at the high gas concentration range (i.e. the detection value varies in proportion to the logarithmic value of the gas concentration) and also good sensitivity (resistance value variation) at the relatively low gas concentration range.

Moreover, with this sensor, its sensitivity for $H_2$ is small, and this selectively against $H_2$ may be maintained at a high temperature where the effect of moisture is negligible.

Figure 7:
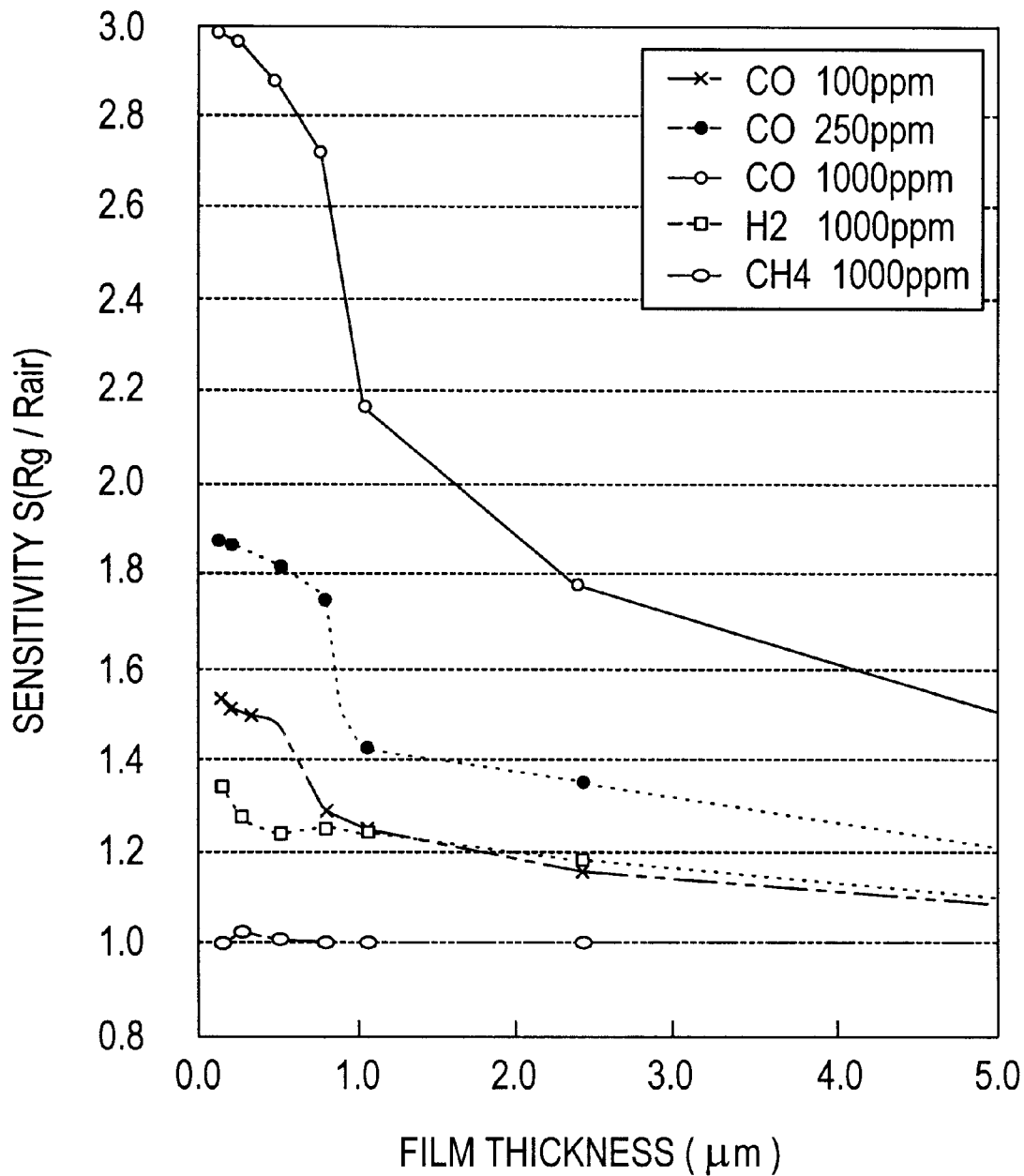
FIG. 7 is a graph illustrating relationship between film thickness and sensitivity of the sensor including the gas detecting portion having the Composition 2.

FIG. 7 illustrates the result of study of relationship between the film thickness and the sensitivity of the sensor including the gas detecting portion comprised of the material of this Composition 2 (specifically, 100% substitution by Y, i.e. b=1). In this graph, the horizontal axis represents the film thickness (μm) and the vertical axis represents the sensitivity S. As may be apparent from the results shown, the sensitivity depends on the film thickness. When the film thickness is smaller than 1 μm, the CO sensitivity is significantly increased, so that the selectivity against $H_2$ may be maintained sufficiently. The present inventors believe that this phenomenon is attributable to increase of the effect of CO on the resistance variation of the gas detecting portion in association with decrease in the film thickness. The lower limit of the film thickness is the detectable limit of electric resistance value. The same tendency was observed also in the cases having different substitution amounts.

Embodiments of Composition 3

(gas detecting portion comprised mainly of copper oxide semiconductor added with a metal compound belonging in group 2A of the periodic table)

[example fabrication of gas detection portion]

As material for forming the gas detecting portion, commercially available CuO powder, as Cu source, was employed, and to this, powder of a compound of metal belonging in the group 2A of the periodic table, preferably, an alkaline earth metal compound, more preferably, $CaCO_3$, $SrCO_3$, $BaCO_3$, is added in a predetermined ratio. Then, this mixture is heated at 600 to 1000° C. to be rendered into a sintered product to be used as the gas detecting portion. The sintering is effected, preferably, on the substrate. Then, on this gas detection portion, the electrodes are disposed with a predetermined inter-distance.

[embodiment 1 of Composition 3]

As the raw material of the gas detecting portion, commercially available CuO powder of high purity was employed as the Cu source, and $BaCO_3$ was used as the Ba compound raw material. And, these materials were mixed to obtain a predetermined Ba/Cu ratio. Then, the mixture was heated at 600 to 960° C., whereby the gas detecting portion was obtained as the sintered product. Incidentally, the equivalent weight ratio of Ba/Cu was varied in the range of 0 to 2. The equivalent ratios of Ba/Cu actually used were 0.0005, 0.001, 0.005, 0.01, 0.03, 0.05, 0.11, 0.67, 1.0 and 2.0. For comparison, a system with no addition of Ba compound was also studied. The gas detecting portions thus obtained were analyzed by the X-ray diffraction analysis. The analysis revealed that the crystal phase of the sintered products were comprised mainly of CuO and $BaCuO_2$ and also that $BaCO_3$ was also observed in the case of those having a large addition amount of Ba or treated under low temperature.

On one side of the above gas detecting portion, electrodes were provided by using platinum as the raw material thereof. And, a heating substrate was fixedly attached to the other side of the gas detecting portion, whereby the gas detecting sensor element was obtained.

[embodiment 2 of Composition 3]

Ca/Cu type gas detecting portion was fabricated under the same conditions as the embodiment 1 of Composition 3, except that CaCO$_3$ was employed as the Ca compound raw material in this case. However, the sintering temperature was between 600 and 960° C.

The equivalent weight ratios of Ca/Cu actually used were 0.0005, 0.001, 0.005, 0.01, 0.03, 0.05, 0.1, 0.2, 0.5 and 2.0. For comparison, a system with no addition of Sr compound was also studied. The gas detecting portions thus obtained were analyzed by the X-ray diffraction analysis. The analysis revealed that the crystal phase of the sintered products were comprised mainly of CuO, Ca$_2$CuO$_3$ and also that CaCO$_3$ phase was also observed in the case of those having a large addition amount of Ca or treated under low temperature.

In this embodiment too, like the embodiment 1 of Composition 3 described above, the electrodes and substrate were provided, whereby a gas sensor element was obtained.

[embodiment 3 of Composition 3]

Sr/Cu type gas detecting portion was fabricated under the same condition as the embodiment 1 of Composition 3, except that SrCO$_3$ was employed as the Sr compound raw material in this case.

The equivalent weight ratios of Sr/Cu actually used were 0.0005, 0.001, 0.005, 0.01, 0.03, 0.05, 0.11, 0.5, 1.0 and 2.0. For comparison, a system with no addition of Sr compound was also studied. The gas detecting portions thus obtained were analyzed by the X-ray diffraction analysis. The analysis revealed that the crystal phase of the sintered products were comprised mainly of CuO, CuSrO$_2$, Cu$_2$SrO$_3$ and also that SrCO$_3$ phase was also observed in the case of those having a large addition amount of Sr or treated under low temperature.

In this embodiment too, like the embodiment 1 of Composition 3 described above, the electrodes and substrate were provided, whereby a gas sensor element was obtained.

In the above experiment, the lower limit of the addition amount of the 2A group metal compound was 0.0005 (0.05%) in the disclosed embodiment. However, this limit was imposed due to the use of high-purity copper oxide (99.99%) readily available at present. Hence, it is understood that the limit may be still lower.

[measurement of sensitivity]

Target gas for detection was obtained by mixing CO and H$_2$ in predetermined concentrations with air and by adding thereto a predetermined amount of water vapor. The gas had an oxygen concentration of about 10% and a volume ratio of water vapor of about 10% (about 80 g/m$^3$ if converted into the absolute humidity).

In the measurement conducted, a predetermined electric potential was applied to the substrate whose gas detecting portion was heated and maintained at 250 to 450° C. And, gas concentration detection was made by measuring electric resistance developed between the opposed electrodes. The gas sensitivity (S) was calculated in the manner described hereinbefore.

As for the operating temperature of the sensor, for all of the gas detecting portions, the higher the temperature, the lower its CO sensitivity. Conversely, if the temperature is lower than 250° C., the response speed becomes slower. Therefore, the optimal temperature range is between 300 and 350° C.

Table 2 shows the results of measurements of the sensitivities of the gas sensor elements obtained in the embodiments 1 through 3 of Composition 3 described above for the target gas containing either CO or H$_2$.

TABLE 2

| group 2A metal/Cu | Ba | | Ca | | Sr | |
|---|---|---|---|---|---|---|
| equivalent weight ratio | CO sensitivity | H$_2$ sensitivity | CO sensitivity | H$_2$ sensitivity | CO sensitivity | H$_2$ sensitivity |
| 0.0000 | 1.36 | 1.78 | 1.36 | 1.78 | 1.36 | 1.78 |
| 0.0005 | 1.59 | 1.19 | 1.57 | 1.41 | 1.44 | 1.32 |
| 0.001 | 1.39 | 1.11 | 1.52 | 1.36 | 1.30 | 1.10 |
| 0.005 | 1.11 | 1.06 | 1.15 | 1.13 | 1.22 | 1.07 |
| 0.01 | 1.22 | 1.12 | 1.04 | 1.02 | 1.15 | 1.05 |
| 0.03 | 1.02 | 1.00 | 1.05 | 1.01 | 1.17 | 1.02 |
| 0.05 | 1.24 | 1.00 | 1.05 | 1.02 | 1.18 | 1.00 |
| 0.1 | 1.20 | 1.02 | 1.04 | 1.00 | — | — |
| 0.111 | — | — | — | — | 1.20 | 1.03 |
| 0.2 | — | — | 1.08 | 1.00 | — | — |
| 0.5 | — | — | 1.27 | 1.00 | 1.14 | 1.02 |
| 0.67 | 1.44 | 1.05 | — | — | — | — |
| 1.0 | 1.66 | 1.03 | — | — | 1.13 | 1.07 |
| 2.0 | 1.50 | 1.00 | 1.07 | 1.00 | 1.11 | 1.02 |

In the above Table 2, the column: "Ba" shows the dependence of the sensitivity S of the Ba type copper oxide sensor element of the embodiment 1 of Composition 3 on the addition amount of Ba, for the target gas containing 1000 ppm of CO and the target gas containing 1000 ppm of H$_2$.

From these results, the followings will be understood. Namely, with addition of a trace amount of Ba as small as Ba/Cu ratio of about 0.0005, the H$_2$ sensitivity is reduced significantly, so that the CO sensitivity becomes much higher than the H$_2$ sensitivity. When Ba/Cu becomes 0.03 or greater, the ration between the resistance value for 1000 ppm of H$_2$ and 0 ppm of H$_2$ becomes substantially '1', thus the element substantially loses its H$_2$sensitivity. Hence, this element is capable of detecting CO with particularly high selectivity.

In the above Table 2, the column: "Ca" shows the dependence of the sensitivity S of the Ca type copper oxide sensor element of the embodiment 2 of Composition 3 on the addition amount of Ca, for the target gas containing 1000 ppm of CO and the target gas containing 1000 ppm of H$_2$.

From these results, the followings will be understood. Namely, with addition of a trace amount of Ca as small as Ca/Cu ratio of about 0.0005, the H$_2$ sensitivity is reduced significantly, so that the CO sensitivity becomes much higher than the H$_2$ sensitivity. When Ca/Cu becomes about 0.01, the ration between the resistance value for 1000 ppm of $H_2$ and 0 ppm of $H_2$ becomes substantially '1', thus the element substantially loses its $H_2$ sensitivity. Hence, this element is capable of detecting CO with particularly high selectivity.

In the above Table 2, the column: 'Sr' shows the dependence of the sensitivity S of the Ca type copper oxide sensor element of the third composition example 3 on the addition amount of Sr, for the target get containing 1000 ppm of CO and the target gas containing 1000 ppm of $H_2$.

From these results, the followings will be understood. Namely, with addition of a trace amount of Sr as small as Sr/Cu ratio of about 0.0005, the CO sensitivity becomes higher than the $H_2$ sensitivity. When Sr/Cu becomes about 0.03, like the embodiment 1, the $H_2$ sensitivity becomes substantially zero. Hence, this element is capable of detecting CO with particularly high selectivity.

Figure 8:
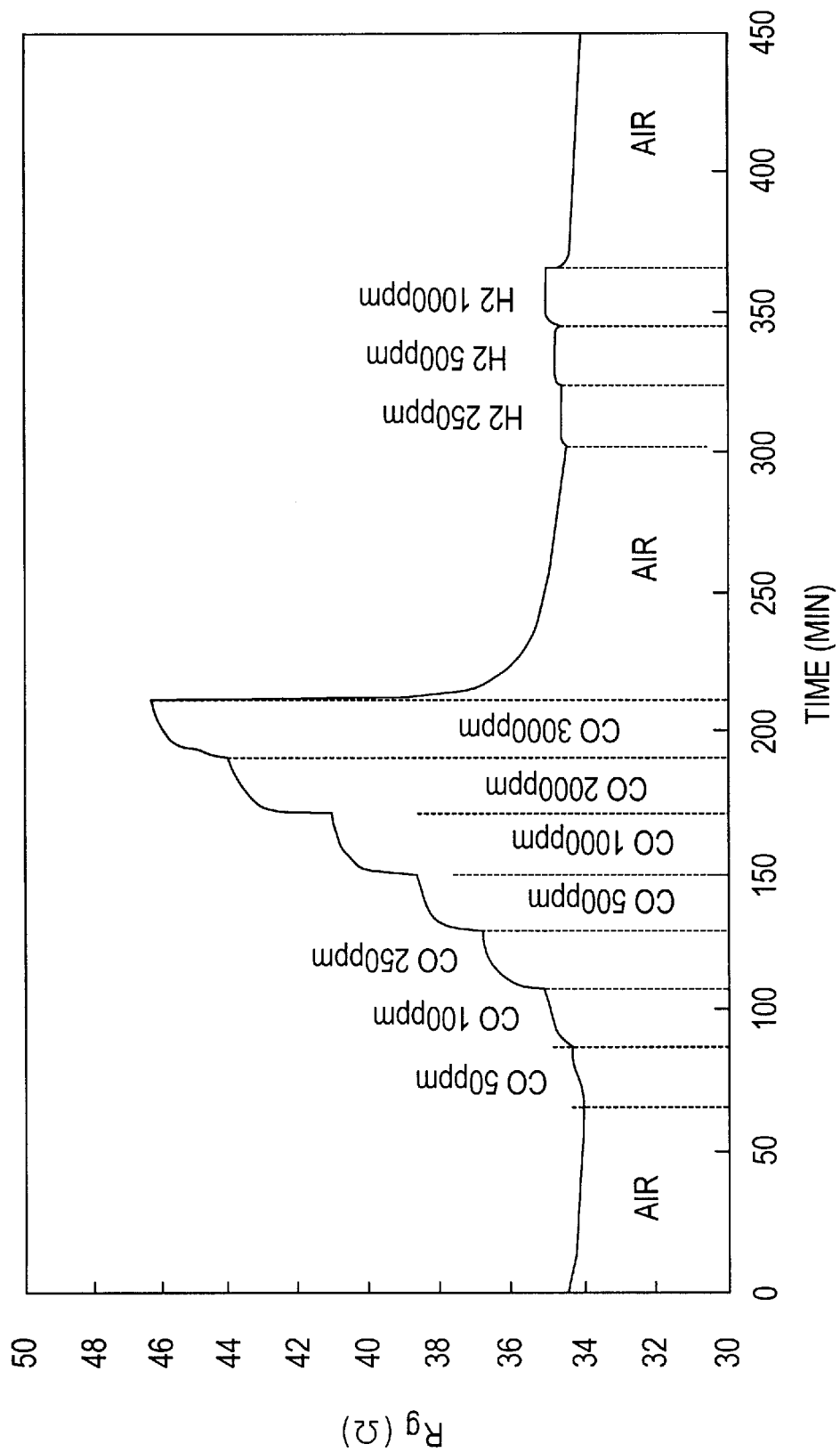
FIG. 8 is a graph illustrating CO and $H_2$ response characteristics of the sensor including the gas detecting portion having the Ca/Cu composition.
Figure 9:
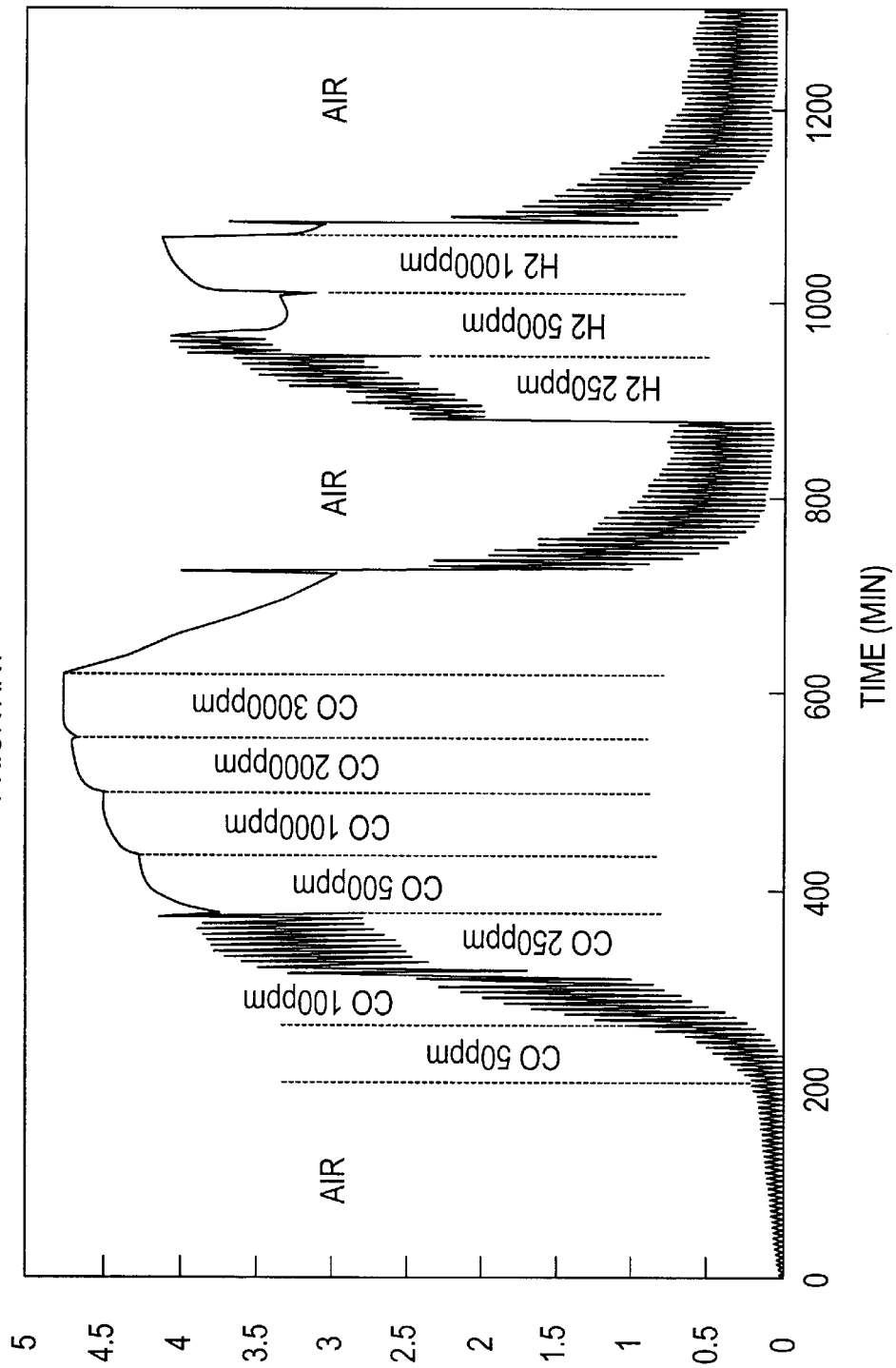
FIG. 9 is a graph illustrating CO and $H_2$ response characteristics of a conventional sensor including a gas detecting portion comprised mainly of tin oxide.

FIG. 8 illustrates the response characteristics, corresponding to FIG. 9, of the sintered product having the Ca/Cu ratio of 1/9 at the water vapor concentration of 1% at 300° C. In this case too, in the measurement, no periodical heating/cooling operation was effected.

The results show that this product is capable of detecting CO without necessitating the periodical heating/cooling operation. And, this product has good quantitative performance at the high gas concentration range (the detection value varies in proportion to the logarithmic value of the gas concentration) as well as good sensitivity (resistance value variation) in the relatively low concentration range.

Moreover, with this sensor, its sensitivity for $H_2$ is small, and the selectivity against $H_2$ may be maintained at the high temperature where the effect of water vapor is negligible.

[other embodiment]

a) As the material for forming the electrodes, it is preferred that such precious metal as gold (Au), silver (Ag), platinum (Pt) be used. In case the sintering method is employed for fabricating the gas detecting portion alone, it is necessary to fixedly attach this to the substrate. And, the heating substrate is attached to the other side of the gas detecting portion opposite to the side including the electrodes. For heating the gas detecting portion, it is also possible to embed a heater within the powderly material when this material is sintered, so that the heater is disposed inside the gas detecting portion to receive power from the outside.

b) In the manufacture of the gas detecting portion, binder material not affecting the sensor sensitivity may be used. Specific examples of such binder material are magnesium oxide (MgO), silica ($SiO_2$), alumina ($Al_2O_3$), and so on.

c) As the catalyst to be used for the gas detecting portion, such precious metal catalyst as Pt, Pd, Rh, Au or the like may be employed, so that the catalyst will be affixed to the surface of the gas detecting portion. In case the gas detection portion is manufactured by the powder sintered method, the catalyst may be mixed with the raw material powder to be sintered together to be attached thereto.

By using such catalyst, the CO sensitivity of the sensor may be further improved.

d) In the foregoing embodiment, for constructing the gas detecting portion of the Composition 2, there were described the results of one having the composition satisfying the expression: a=1−b. However, in the case also of further construction in which 'a' is greater than '0' and smaller than '1' and 'b' is greater than '0' (excluding '0' per se) and smaller than '1', it was found that this further construction too is capable of selectively detecting CO against $H_2$, as described hereinbefore.

e) In constructing the gas detecting portion of the Composition 3, as the material to be added to the copper oxide semiconductor, in addition to Ba, Ca, Sr described in the foregoing embodiments, any other element belonging in the group 2A of the periodic table may employed so as to reduce the $H_2$ sensitivity of the sensor.

The invention may be embodied in other specific forms without departing from the spirit or essential characteristics thereof. The present embodiments are therefore to be considered in all respects as illustrative and not restrictive, the scope of the invention being indicated by the appended claims rather than the foregoing description and all changes which come within the meaning and range of equivalency of the claims are therefore intended to be embraced therein.

What we claim are:

1. A carbon monoxide sensor comprising a gas detecting portion for detecting carbon monoxide and at least a pair of electrodes electrically connected with said gas detecting portion for detecting an electrical change developed in said gas detecting portion, wherein said gas detecting portion comprises at least one metal oxide having the formula $Cu_{1-x}Bi_xO_y$ where 0<x<1 and 1<y<1.5.

2. The carbon monoxide sensor of claim 1, wherein 0<x<0.5.

3. The carbon monoxide sensor of claim 1, wherein said gas detecting portion is formed by a sintering method.

4. The carbon monoxide sensor of claim 1, wherein said gas detecting portion further comprises a binder which does not affect CO sensitivity of the gas detecting portion.

5. The carbon monoxide sensor of claim 1, wherein said gas detecting portion further comprises a catalyst layer for preventing non-CO gas from reaching the gas detecting portion.

6. The carbon monoxide sensor of claim 1, wherein said gas detecting portion further comprises a heater.

7. The carbon monoxide sensor of claim 2, wherein said gas detecting portion is formed by a sintering method.

8. The carbon monoxide sensor of claim 2, wherein said gas detecting portion further comprises a binder which does not affect CO sensitivity of the gas detecting portion.

9. The carbon monoxide sensor of claim 2, wherein said gas detecting portion further comprises a catalyst layer for preventing non-CO gas from reaching the gas detecting portion.

10. The carbon monoxide sensor of claim 2, wherein said gas detecting portion further comprises a heater.

* * * * *

UNITED STATES PATENT AND TRADEMARK OFFICE
CERTIFICATE OF CORRECTION

PATENT NO. : 5,980,833
DATED : November 9, 1999
INVENTOR(S) : Higaki, et al

Page 1 of 2

It is certified that error appears in the above-identified patent and that said Letters Patent is hereby corrected as shown below:

On the title page: Item [56] Foreign Patent Documents, change "6632265" to --0632265"--.

In column 1, line 8, change "substrate" to - - substance - -.
In column 1, line 11, change "is" 2nd Occurrence to --in--.
In column 1, line 37, change "details" to - - detail - -.
In column 1, line 54, change "substantially same" to - - substantially the same - -.
In column 3, line 29, change "tis" to - - its - -.
In column 6, line 18, change "this" to - - the - -.
In column 6, line 24, change "detection" to - - detecting - -.
In column 7, line 13, change "which does contains" to - - which contains - -.
In column 7, line 15, change "place" to - - placed - -.
In column 8, line 31, change "dectection" to - - detecting - -.
In column 8, line 53, change "it" to - - its - -.
In column 9, line 44, change "get" to - - gas - -.

UNITED STATES PATENT AND TRADEMARK OFFICE
CERTIFICATE OF CORRECTION

PATENT NO. : 5,980,833
DATED : November 9, 1999
INVENTOR(S) : Higaki, et al

It is certified that error appears in the above-identified patent and that said Letters Patent is hereby corrected as shown below:

In column 10, line 22, change "to increase" to -- to the increase --.
In column 10, line 32, change "detection" to -- detecting --.
In column 10, line 42, change "detection" to -- detecting --.
In column 12, line 48, change "followings" to -- following --.
In column 12, line 55, change "$H_2$sensitivity" to -- $H_2$ sensitivity --.
In column 12, line 63, change "followings" to -- following --.
In column 13, line 9, change "get" to -- gas --.
In column 13, line 11, change "followings" to -- following --.
In column 13, line 54, change "detection" to -- detecting --.
In column 14, line 14, change "may employed" to
-- may be employed --.
In column 14, line 31, change "1<y<1.5" to -- 1<y<1.5, said sensor capable of detecting carbon monoxide --.

Signed and Sealed this

Ninth Day of January, 2001

Attest:

Q. TODD DICKINSON

*Attesting Officer*         *Commissioner of Patents and Trademarks*

UNITED STATES PATENT AND TRADEMARK OFFICE
CERTIFICATE OF CORRECTION

PATENT NO. : 5,980,833
DATED : November 9, 1999
INVENTOR(S) : Higaki, et al.

It is certified that error appears in the above-identified patent and that said Letters Patent is hereby corrected as shown below:

Title page:
In the section entitled Assignee, change "Noritsu Koki Co. Ltd., Wakayama" to --Osaka Gas Co., Ltd., Osaka --.

Signed and Sealed this

Nineteenth Day of June, 2001

*Attest:*

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO.    : 5,980,833
DATED         : November 9, 1999
INVENTOR(S)   : Higaki et al.

It is certified that error appears in the above-identified patent and that said Letters Patent is hereby corrected as shown below:

Title page,
Item [56], References Cited, FOREIGN PATENT DOCUMENTS, change "6632265" to -- 0632265 --.

Column 1,
Line 8, change "substrate" to -- substance --.
Line 11, change "is" 2nd occurrence to -- in --.
Line 37, change "details" to -- detail --.
Line 54, change "substantially same" to -- substantially the same --.

Column 3,
Line 29, change "tis" to -- its --.

Column 6,
Line 18, change "this" to -- the --.
Line 24, change "detection" to -- detecting --.

Column 7,
Line 13, change "which does contains" to -- which contains --.
Line 15, change "place" to -- placed --.

Column 8,
Line 31, change "dectection" to -- detecting --.
Line 53, change "it" to -- its --.

Column 9,
Line 44, change "get" to -- gas --.

Column 10,
Line 22, change "to increase" to -- to the increase --.
Lines 32 and 42, change "detection" to -- detecting --.

Column 12,
Lines 48 and 63, change "followings" to -- following --.
Line 55, change "$H_2$sensitivity" to -- $H_2$ sensitivity --.

UNITED STATES PATENT AND TRADEMARK OFFICE
CERTIFICATE OF CORRECTION

PATENT NO. : 5,980,833
DATED : November 9, 1999
INVENTOR(S) : Higaki et al.

It is certified that error appears in the above-identified patent and that said Letters Patent is hereby corrected as shown below:

<u>Column 13,</u>
Line 9, change "get" to -- gas --.
Line 11, change "followings" to -- following --.
Line 54, change "detection" to -- detecting --.

<u>Column 14,</u>
Line 14, change "may employed" to -- may be employed --.
Line 31, change "1<y<1.5" to -- 1<y<1.5, said sensor capable or detecting carbon monoxide --.

Signed and Sealed this

Twenty-second Day of February, 2005

JON W. DUDAS
*Director of the United States Patent and Trademark Office*